US00PP30164P2

(12) United States Plant Patent
Bean

(10) Patent No.: US PP30,164 P2
(45) Date of Patent: Jan. 29, 2019

(54) ***AGAPANTHUS* PLANT NAMED 'SDB002'**

(50) Latin Name: ***Agapanthus* hybrid**
Varietal Denomination: SDB002

(71) Applicant: Charles Andrew de Wet, Johannesburg (ZA)

(72) Inventor: Quinton Bean, Johannesburg (ZA)

(73) Assignee: Charles Andrew De Wet, Johannesburg (ZA)

( * ) Notice: Subject to any disclaimer, the term of this patent is extended or adjusted under 35 U.S.C. 154(b) by 0 days.

(21) Appl. No.: 15/732,579

(22) Filed: Nov. 29, 2017

(51) Int. Cl.
*A01H 5/02* (2018.01)

(52) U.S. Cl.
USPC ..... Plt./398

(58) Field of Classification Search
USPC ..... Plt./398
See application file for complete search history.

*Primary Examiner* — Annette H Para
(74) *Attorney, Agent, or Firm* — Penny J. Aguirre

(57) ABSTRACT

A new cultivar of *Agapanthus*, 'SDB002', that is characterized by its inflorescences that are born on short flowering stems, its compact plant habit, its dense umbels of flowers that are dark blue in color, and its re-blooming from July to January in South Africa, its very floriferous blooming period producing an unusually high number of inflorescences, and its very floriferous blooming habit; producing numerous inflorescences.

2 Drawing Sheets

Botanical classification: *Agapanthus* hybrid.
Varietal denomination: 'SDB002'.

BACKGROUND OF THE INVENTION

The present invention relates to a new and distinct cultivar of *Agapanthus* of hybrid origin and will be referred to hereafter by its cultivar name, 'SDB002'. 'SDB002' represents a new perennial grown for landscape use.

The new cultivar was derived from a controlled breeding program by the Inventor in Hartebeespoort, Northwest Province, South Africa. The objective of the breeding program is to develop new cultivars of *Agapanthus* that are medium in size and produce a high number of inflorescences on short bloom stalks. The Inventor made a cross in November of 2009 between unnamed proprietary plants of *Agapanthus* from the Inventor's breeding program as both the female parent and male parent The Inventor selected 'SDB002' in November of 2011 as a single unique plant amongst the seedlings that resulted from the above cross.

Asexual propagation of the new cultivar was first accomplished by division by the Inventor in Hartebeespoort, Northwest Province, South Africa in January of 2013. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'SDB002' as a distinct cultivar of *Agapanthus*.

1. 'SDB002' exhibits inflorescences that are born on short flowering stems.
2. 'SDB002' exhibits a compact plant habit.

3. 'SDB002' exhibits dense umbels of flowers that are dark blue in color.
4. 'SDB002' exhibits a very floriferous blooming habit; producing numerous inflorescences.

The female parent of 'SDB002' differs from 'SDB002' in producing much fewer inflorescences. The male parent of 'SDB002' differs from 'SDB002' in having a larger plant eight and flowers that are pale blue in color. 'SDB002' can be most closely compared to the *Agapanthus* cultivars 'ANDBIN' (U.S. Plant Pat. No. 26,336) and 'Benfran' (U.S. Plant Pat. No. 21,705). 'ANDBIN' is similar to 'SDB002' in having high inflorescence production. 'ANDBIN' differs from 'SDB002' in having flowers that are lighter blue in color. 'Benfran' is similar to 'SDB002' in having a compact plant habit. 'Benfran' differs from 'SDB002' in having flowers that arc pale blue in color.

BRIEF DESCRIPTION OF THE DRAWINGS

The accompanying colored photographs illustrate the overall appearance and distinct characteristics of the new *Agapanthus*. The photographs were taken of plants about 2 years in age (from a bare root division) of 'MDB001' as grown outdoors in a 3-gallon container in Hartebeespoort, Northwest Province, South Africa.

The photograph in FIG. 1 provides a side view of a plant of 'SDB002' in bloom.

Figure 1:
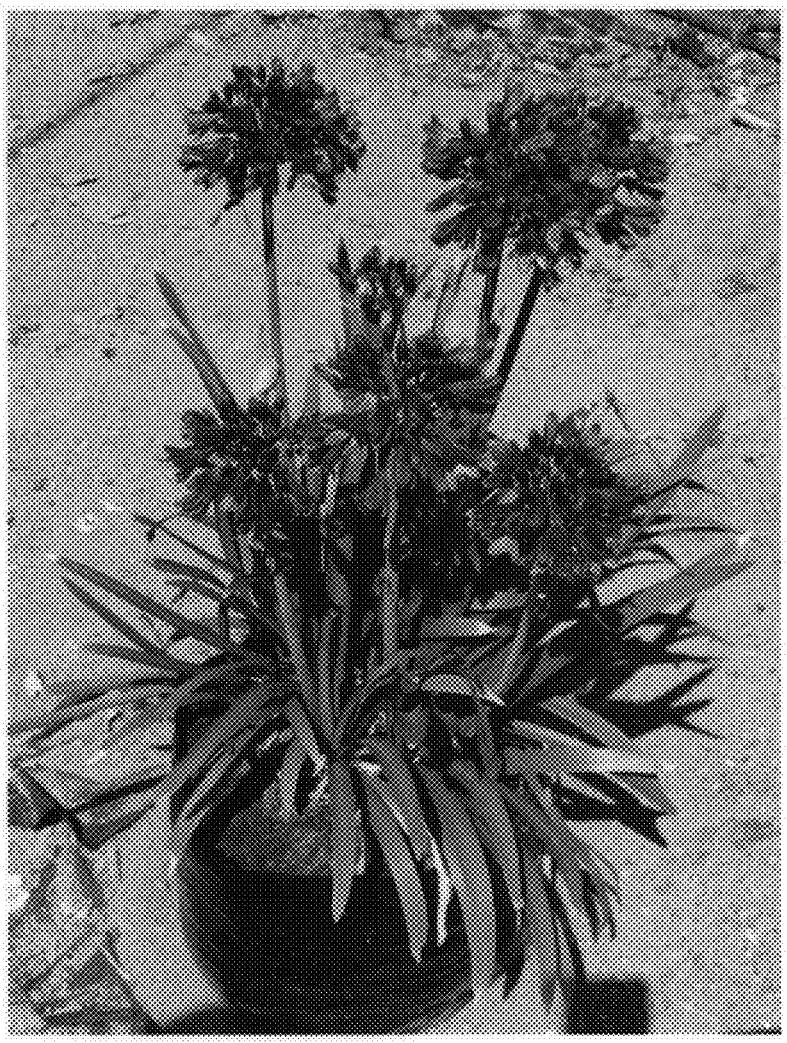
Figure 2:
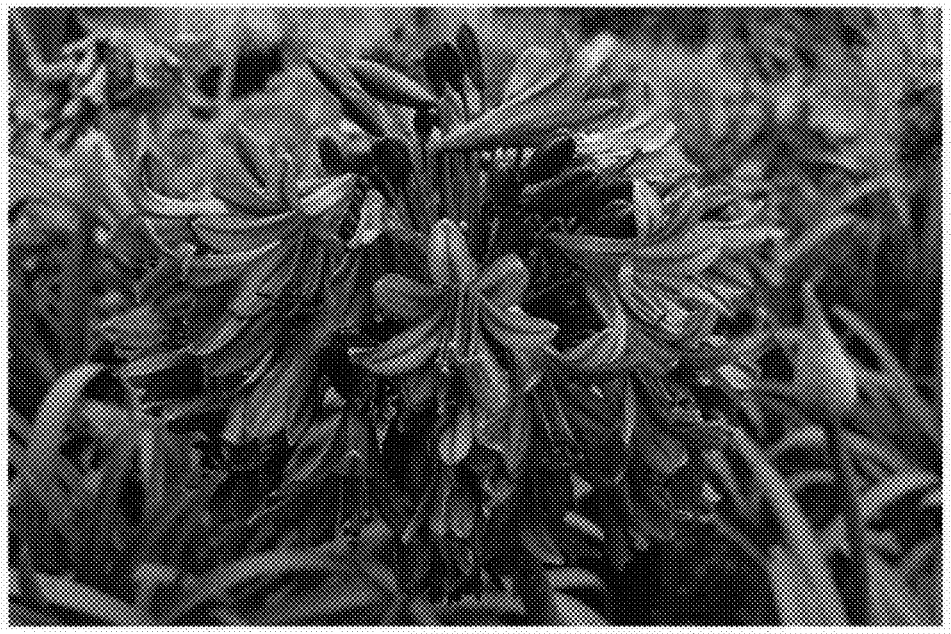

The photograph in FIG. 2 provides a close-up view of an inflorescence of 'SDB002'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 1 year-old plants (from a bare root division) of 'SDB002' as grown outdoors in 3-gallon containers in Loxley, Ala. The phenotype of the new cultivar may vary with variations in environmental, climatic, and cultural conditions, as it has not been tested under all possible environmental conditions. The color determinations are in accordance with The 2015 R.H.S. Colour Chart of The Royal Horticultural Society, London, England, except where general color terms of ordinary dictionary significance are used.

General description:

*Blooming period.*—Early to mid summer in South Africa.

*Plant type.*—Semi-deciduous (climate dependent) herbaceous perennial.

*Plant habit.*—Compact, basal rosettes with inflorescences emerging from the rosette center.

*Height and spread.*—25 to 35 cm (foliage height) and 35 to 45 (including inflorescences) and 45 cm in spread.

*Cold hardiness.*—At least to U.S.D.A. Zone 8.

*Diseases.*—Good resistance has been observed to root and crown rot caused by *Fusarium* sp. and soft rot caused by *Erwinia* sp.

*Root description.*—Thick and fleshy, 161C in color.

*Propagation.*—Tissue culture (preferred) and division.

*Growth rate.*—Vigorous.

*Number of shoots (rosettes).*—An average of 10 as grown in a 3-gallon container.

Foliage description:

*Leaf shape.*—Ligulate.

*Leaf division.*—Simple.

*Leaf base.*—Truncate.

*Leaf arrangement.*—2-ranked, arranged in shoots an average of 1 cm diameter at base.

*Leaf apex.*—Narrow acute.

*Leaf aspect.*—Emerging leaves erect, then cascade.

*Leaf venation.*—Parallel, upper surface; matches leaf coloration, and lower surface; with only mid rib on lower surface conspicuous; a color ranging between 138B towards the apex to 145D near the base.

*Leaf margins.*—Entire.

*Leaf size.*—Up to 47 cm in length and up to 2.5 cm in width.

*Leaf surface.*—Smooth, glabrous, and dull on upper and lower surface.

*Leaf number.*—Average of 8 leaves per rosette.

*Leaf color.*—Young leaves, upper and lower surface; 138A and blending to 137A near apex and 145D at base, mature leaves upper surface; 137A and 145B near base with very base N145D and slightly suffused with 155A, mature leaves lower surface; 138A and 144D near base with very base heavily suffused with 145D with margins 144A.

*Leaf attachment.*—Sessile to base.

Flower description:

*Inflorescence type.*—Dense umbel.

*Flower fragrance.*—None.

*Flower type.*—Rotate, campanulate, base of tepals fused.

*Flower number.*—An average of 100 flowers per umbel.

*Inflorescence size.*—Average of 15 cm in height and diameter.

*Flower size.*—An average of 3.5 cm in depth and 3 cm in diameter.

*Lastingness of inflorescence.*—Average 7 days.

*Flower aspect.*—Upward to downward.

*Peduncle.*—1 per rosette, very strong, oval in shape, held primarily upright, average of 50 cm in length and 1 cm in width at distal region and 1.5 cm in width at proximal region, a blend of 144A and 144B in color with base 145B and slightly, satiny and glabrous.

*Pedicels.*—Very strong, average of 4 cm in length and 2 mm in width, held erect to outward (0° to 180°), 144C in color, glabrous surface.

*Flower buds.*—Obelliptic in shape, average of 2 cm in length and 7 mm in width, a blend of 93B in color with slight markings of 145D, enclosed by 2 to 3 deciduous spathe-like bracts that split open and drop when flowers open; ovate to lanceolate in shape, acuminate apex, truncate base, up to 6.5 cm in length and 2.5 cm in width, color outer surface; 146C and suffused with 145D at base, color inner surface; a blend of 148B and striations of 148B, glabrous and dull on both surfaces, spathe prior to opening; ovate-lanceolate in shape with acute and reflexed apex, an average of 5 cm in length and 2.5 cm in diameter.

*Tepals.*—6 lobes rotate, oblanceolate in shape, lower 40% fused, entire margins, broadly acute apex, glabrous and satiny on inner and outer surfaces, thick substance, an average of 3 cm in length and 7 mm in width, color on both surfaces; a blend of N89C, N88C and N88D with center vein on inner surface N89C, tube portion is an average of 2 cm in length and 7 mm in width.

Reproductive organs:

*Gynoecium.*—1 pistil, average of 2.2 cm in length, stigma is narrow clavate in shape and 85A in color, style is 1 cm in length and ranges in color from 85D at base to 86C at apex, ovary is obelliptic in shape, 1 cm in length, 5 mm in width and 145C in color.

*Androecium.*—6 stamens, anthers are dorsifixed, oblong in shape, average of 0.5 cm in length, and 11B in color, filament is 1.3 cm in length and N88B suffused with 88A in color, 2-Staminoids; average of 2, falcate in shape, 1.5 cm in length, 4 mm in width, color ranging 84D at base to N89B at Apex, with undeveloped anther adhered at apex, pollen is moderately abundant in quantity and 17C in color.

*Fruit/seed.*—Have not been observed to date.

It is claimed:

1. A new and distinct cultivar of *Agapanthus* plant named 'SDB002' as herein illustrated and described.

* * * * *